US00PP35809P2

(12) United States Plant Patent
Hansen

(10) Patent No.: US PP35,809 P2
(45) Date of Patent: May 14, 2024

(54) ***ECHINACEA* PLANT NAMED 'WATERMELON SUGAR'**

(50) Latin Name: ***Echinacea* hybrid**
Varietal Denomination: Watermelon Sugar

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 18/445,347

(22) Filed: Jul. 25, 2023

(51) Int. Cl.
*A01H 5/02* (2018.01)
*A01H 6/14* (2018.01)

(52) U.S. Cl.
USPC ..... Plt./428

(58) Field of Classification Search
USPC ..... Plt./428

CPC ... A01H 5/02; A01H 5/00; A01H 6/14; A01H 6/1448

See application file for complete search history.

(56) References Cited

U.S. PATENT DOCUMENTS

PP24,354 P2 * 3/2014 Korlipara ..... A01H 5/02 Plt./428

* cited by examiner

*Primary Examiner* — June Hwu

(57) ABSTRACT

The new and distinct cultivar of *Echinacea* plant named 'Watermelon Sugar' of heavily branched plants, strong-stemmed, producing faintly fragrant inflorescences with wide ray florets magenta pink color transitioning to raspberry sherbet coloring and drooping and maturing to a light pinkish color. The center disk florets of watermelon-magenta produce a large center pompon. The new plant has dark-green ovate foliage, produces flowers from mid-summer to late summer, and is suitable as a potted plant, for the landscape, and for cut flower arrangements.

2 Drawing Sheets

Botanical denomination: *Echinacea* hybrid.
Cultivar designation: 'Watermelon Sugar'.

STATEMENT REGARDING PRIOR DISCLOSURES UNDER 37 CFR 1.77(B)(6)

The first non-enabling disclosures of the claimed plant, in the form of a photograph and brief description on a website operated by Walters Gardens, Inc. on Feb. 1, 2023, followed by a photograph and brief description in the "Walters Gardens 2023-2024 Catalog" on May 19, 2023. The claimed plant was first offered for sale on Mar. 1, 2023. No plants of *Echinacea* 'Watermelon Sugar' have been sold in this country or anywhere in the world, nor has any disclosure of the new plant been made, more than one year prior to the filing date of this application, and such sale or disclosure within one year was either derived directly or indirectly from the inventor and therefore a 35 U.S.C. § 102(b) exception.

BACKGROUND OF THE INVENTION

The present invention relates to the new and distinct cultivar of Coneflower from the genus *Echinacea* and given the cultivar name 'Watermelon Sugar'. The new plant was the result of a cross by the inventor of an unnamed proprietary hybrid known as 18-28-11 (not patented) as the female parent and an unnamed proprietary hybrid known as 18-39-2 (not patented) as the male in the summer of 2019, at a wholesale perennial nursery in Zeeland, Michigan. The single seedling selected was evaluated initially in trials in the summer of 2020 at the same nursery and assigned the breeder code of 19-3-6.

*Echinacea* 'Watermelon Sugar' has been asexually propagated at the same nursery by crown division and also using careful shoot tip tissue culture procedures and found to reproduce plants that exhibit all the characteristics identical to the original plant in successive generations.

*Echinacea* 'Watermelon Sugar' is distinct from all other Coneflowers known to the inventor. The nearest comparison cultivars are: 'Butterfly Kisses' U.S. Plant Pat. No. 24,458, 'Strawberry Mousse' (not patented), 'Razzmatazz' U.S. Plant Pat. No. 13,894, 'Delicious Candy' (not patented), 'Secret Affair' U.S. Plant Pat. No. 24,354, and 'Rainbow Sherbet' U.S. Plant patent application Ser. No. 17/803,932.

'Butterfly Kisses' has a shorter habit with smaller inflorescences having light-pink ray florets and deeper pink disk florets that stay close to the same colors through maturity. 'Strawberry Mousse' is taller in habit, with inflorescences having ray florets of a lighter purplish-pink color that droop more, and the disk pompon is smaller and a lighter purplish-pink. 'Razzmatazz' is much taller in habit, has peduncles with less branching, smaller inflorescences with light pinkish-purple ray florets, and a slightly lighter center pompom of medium purplish-pink disk florets. 'Delicious Candy' has a taller habit, with smaller inflorescences, the horizontally-held ray florets are a bright fuchsia color, and the disk florets are a reddish-orange. 'Secret Affair' has a shorter and less branching habit, inflorescences with a single row of more drooping ray florets with a deeper purplish-red color. 'Rainbow Sherbet' has more orangish-red ray florets when initially opening that mature to a more coral pink.

The female parent plant, 18-28-11, has double flowers of salmon-colored with fewer flowers per plant. The male parent plant, 18-39-2, has single reddish flowers with a taller habit.

SUMMARY OF THE INVENTION

*Echinacea* 'Watermelon Sugar' has not been evaluated under all possible environmental conditions. The phenotype may vary with variations in the environment including: growing temperature, available sunlight, nutrients, water, etc. without a change in the genotype of the plant. The new plant is distinct from its parents and all other *Echinacea* known to the applicant in the following combined traits:

1. Faint fragrant inflorescences with ray florets opening magenta-pink;
2. Wide ray florets transition to light-pink drooping slightly;
3. Center pompon of watermelon pink disk florets that have notched apices;
4. Vigorous, compact, growth habit with heavy branching, and strong stems;
5. Dark-green ovate foliage.

BRIEF DESCRIPTION OF THE DRAWINGS

The photographs of 'Watermelon Sugar' demonstrate the overall appearance of the plant including the unique traits. The drawings of the new plant are of a two-year-old plant grown in a full-sun trial garden in Zeeland, Michigan. The colors are as accurate as reasonably possible with color reproductions. Some slight variations of color may occur as a result of lighting quality, intensity, wavelength, direction, or reflection.

DETAILED DESCRIPTION OF THE PLANT

Figure 1:
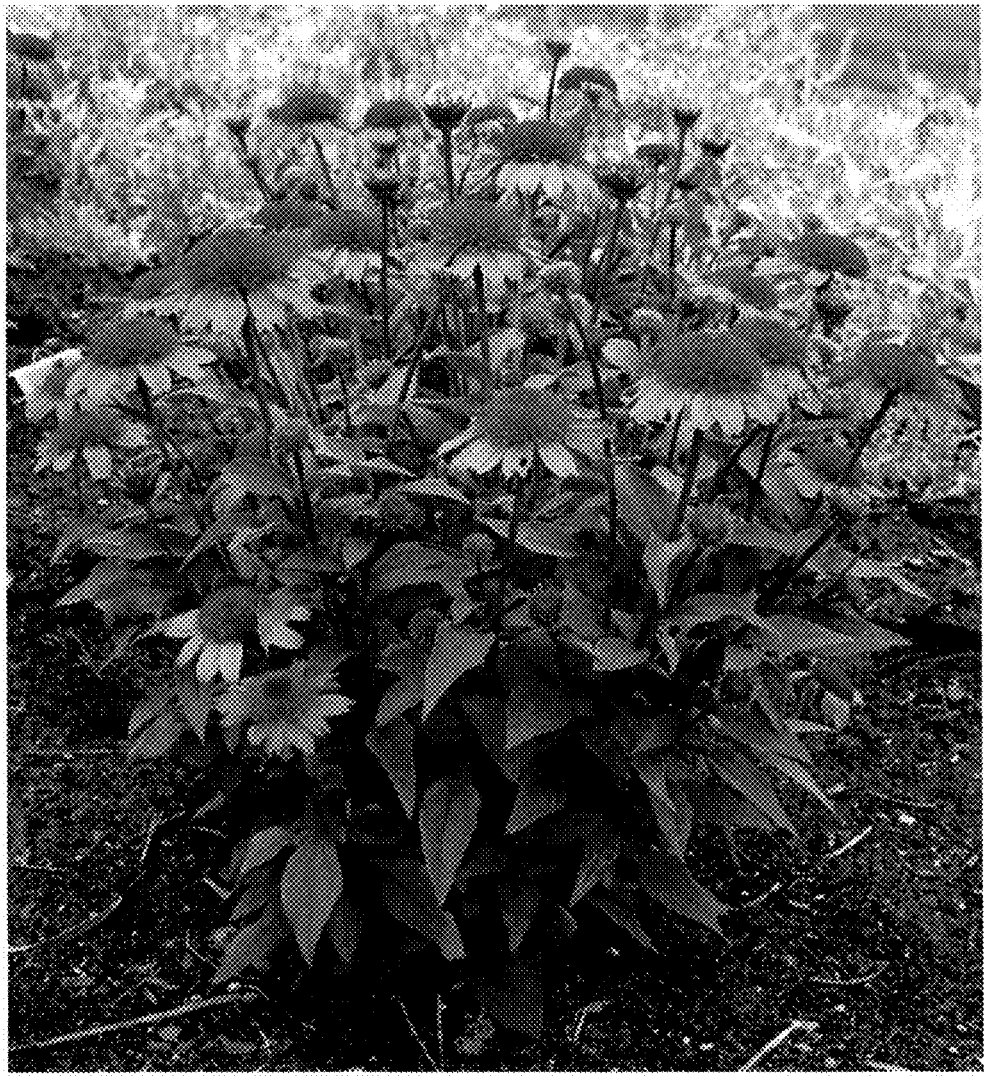
FIG. 1 shows the landscape habit of the new plant in the flower.
Figure 2:
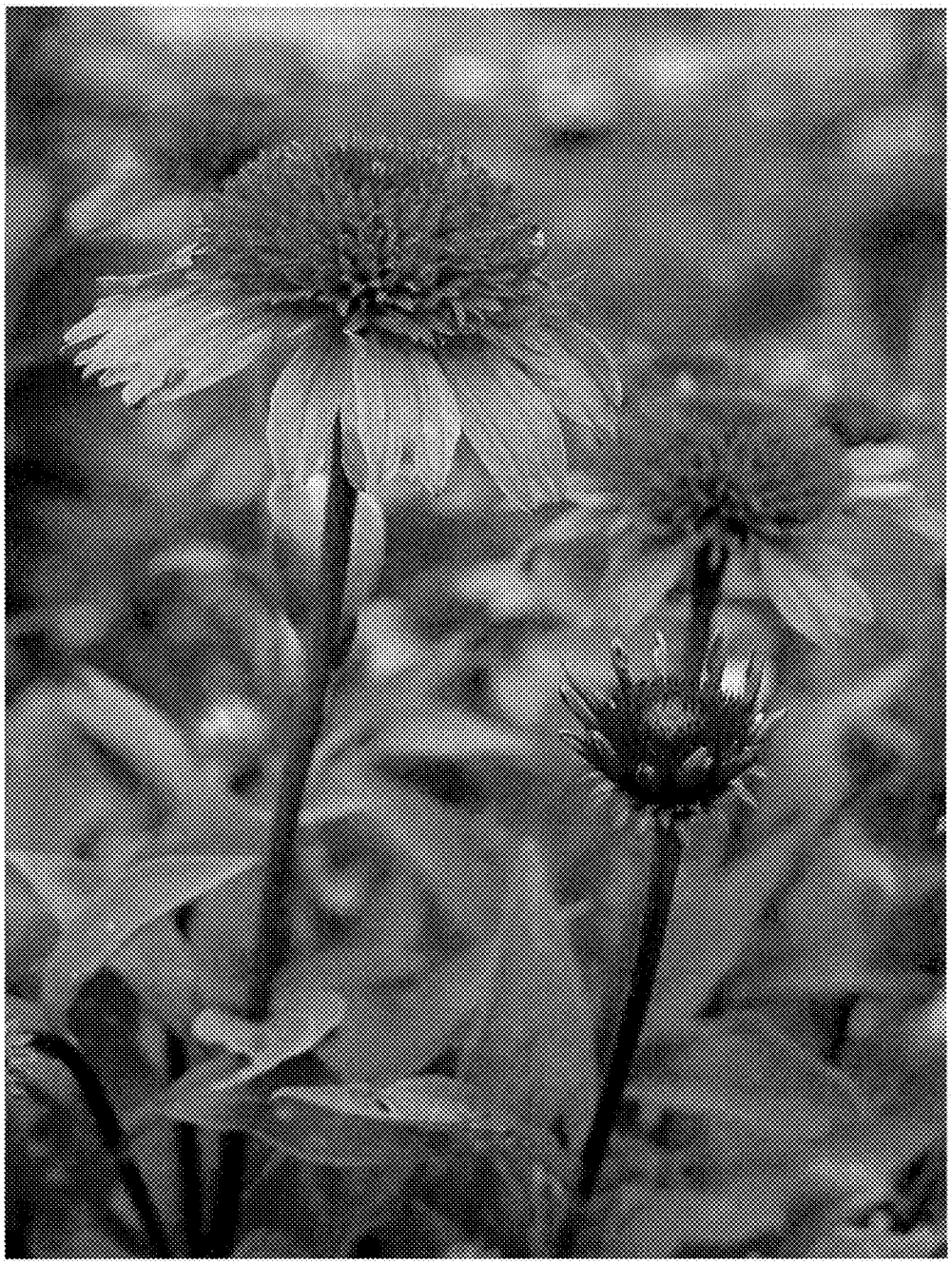
FIG. 2 shows a close-up of some inflorescences with ray florets at various stages of color and large center pompon.

The following description of *Echinacea* 'Watermelon Sugar' is based on observations of two-year-old specimens grown in a partially-shaded greenhouse and in a full-sun trial garden in Zeeland, Michigan. The new plant has not been tested in all environments and some phenotypic differences may occur with different environments without, however, any change in genotype. The color descriptions are based on the 2015 edition of The Royal Horticultural Society Colour Chart except where common dictionary descriptions are used.

Parentage: Female or seed parent is the proprietary unreleased hybrid 18-28-11 and male parent is the proprietary unreleased hybrid 18-39-2; both parents comprising complex crosses with 'Solar Flare' U.S. Plant Pat. No. 22,133, 'Little Annie' (not patented), 'Julia' U.S. Plant Pat. No. 24,629, 'Cleopatra' U.S. Plant Pat. No. 24,631, and 'Butterfly Kisses' U.S. Plant Pat. No. 24,458;

Plant habit: Multi-stemmed, freely-branched, hardy herbaceous perennial, flowering to about 63.5 cm tall and 58 cm wide with foliage to 52 cm tall and 48 cm wide;

Growth rate: Vigorous, finishing in 4-liter containers in about 2 months during the summer;

Roots: Cream-colored, finely-branched;

Foliage: Alternate; ovate; acute apex; cuneate base; margin entire and micro-ciliolate; micro-hirsutulous adaxial and abaxial; to about 12 cm long and 5.5 cm wide decreasing distally, average about 9.5 cm long and 4 cm wide;

Leaf color: Young leaves adaxial nearest RHS 137A, abaxial between RHS 146A and RHS 138A; mature leaves adaxial between RHS 137A and RHS NN137A, abaxial between RHS 137B and RHS 146A; variegation absent;

Foliage fragrance: Not observed;

Venation: Pinnately three-nerved; abaxial midrib and veins costate; glabrous adaxial, hirsutulous abaxial;

Vein color: Adaxial basal midrib and basal primary veins between RHS 154D and RHS 145C, distal primary veins and secondary veins between RHS NN137A and RHS 137A; abaxial midrib and primary veins nearest RHS 145C, secondary veins RHS 147B;

Petiole: Concavo-convex; glabrous adaxial; hirsutulous abaxial; to about 6.5 cm long and 9 mm wide at the semi-clasping base and 4 mm wide in middle of lowest leaves, distal foliage decreasing to nearly sessile;

Petiole color: Adaxial center between RHS 154D and RHS 145C, margin nearest RHS 137A; abaxial center between RHS 137B and RHS 146A, edge between RHS 137B and RHS 146A;

Stem: Hirsutulous; terete, fistulous; strong; stiff; to about 63.5 cm long including peduncle and about 9 mm diameter at base; average 59 cm long and 8 mm diameter; about 7 per plant; aspect upright;

Stem color: Base nearest RHS 146C, above portion nearest RHS 187A;

Peduncle: Hirsutulous to pubescent; cylindrical; strong; stiff; branched; to about 11.5 cm long and 7 mm diameter above last leaves; quantity per stem about six to ten; aspect strongly ascending;

Peduncle color: Nearest RHS 187A;

Internode: 11 to 13 per stem; average about 4.1 cm long, shorter proximally and longer distally; node color same as surrounding peduncle;

Branches: Cylindrical; hirsutulous; tightly angled to main stem to about 60° above horizontal: about six to ten branches per stem; to about 17 cm long and 4 mm diameter;

Branch color: Nearest RHS 187A;

Inflorescence: Bracteate head, aggregate of achene; with single whorl of distinct ligulate ray florets and enlarged disk florets above pappus producing a pompon effect; flowering mid-summer to late summer; initial inflorescence largest, to about 11 cm wide, with inner pompon to 6 cm across and 4.5 cm tall; to six to ten inflorescences per stem;

Inflorescence fragrance: Faint, lightly sweet, honey-like;

Flower persistence: Remaining effective in color for 10 to 14 days depending on temperatures, cone drying on the plant, and effective into winter;

Involucre: With numerous bracts, about 60 to 75 per inflorescence in 3 to 4 whorls; arcuate downward toward peduncle;

Involucre bracts: Deltoid; acute apex; truncate base; ciliolate margin; reflexed; adaxial glabrous to micro-puberulent; abaxial hirsutulous; to about 11 mm long and 3 mm across decreasing distally; color adaxial center nearest RHS 137B, adaxial edges nearest RHS NN137B, and abaxial nearest RHS 137A;

Inflorescence buds with ray florets vertical and still enrolled: About 34 mm across and 22 mm tall; ray floret adaxial color nearest RHS N186D, abaxial color nearest RHS N186D with apical 1 to 2 mm nearest RHS 148C, disk florets nearest RHS 146A in center and perimeter nearest RHS 145C with a blush of nearest RHS 58D, and spines nearest RHS 185A at apices, distal portion nearest RHS N172D, and center and proximally nearest RHS 145A;

disk florets to about 12 mm long, 2 mm wide at apex, and 1.5 mm wide at base; disk floret bud color center nearest RHS 161B, base nearest RHS 145A and apices nearest RHS 182D;

Ray florets: Ligulate; zygomorphic; arrangement in a single moderately imbricate whorl; apex emarginated with two notches to 2 mm deep; base attenuate; margin entire; adaxial and abaxial surfaces matte; 16 to 22 per inflorescence; opening to horizontal, drooping up to 45 degrees below horizontal with maturity; flat, twisting absent; pistillate; ray floret ligule to 44 mm long and 20 mm wide near middle, base 2 mm wide; average size 38 mm long, 16 mm wide at center tapering to 2 mm wide at base; adaxial veins thickened and slightly sulcate;

Ray floret color: Changing with maturity; when first horizontal young adaxial nearest RHS 50B and abaxial nearest RHS 59D with veins nearest RHS 160D, apex nearest RHS 145B and base nearest RHS 145A; in mid-open period adaxial between RHS 59D and RHS 60C, abaxial nearest RHS 51D; before dropping adaxial between RHS 54D and RHS 63C, abaxial between RHS 59D and RHS 64D; basal 2 mm remaining constant between RHS 146D and RHS 145A in both adaxial and abaxial;

Disk florets: About 400 to 500 per inflorescence; zygomorphic; perfect; produced in a large, raised dome about 6.4 cm across and 3.5 cm tall; individually to about 25 mm long, 11 mm across at apex, and 2 mm diameter at base;

*Disk floret corolla*.—Typically five tepals fused forming tube; to about 21 mm long and 11 mm wide at apex, fused in basal 14 mm, free in distal 7 mm; individual tepals about 2 mm wide at fusion; acute apex; entire margin; both surfaces slightly lustrous.

*Disk floret corolla tube color*.—Prior to opening nearest RHS 59B; upon first opening and at maturity color unchanged; adaxial distally nearest RHS 59C, center nearest RHS 47D, and proximally between RHS 148B and RHS 146C; abaxial between RHS 59D and RHS 58D with base between RHS 146D and RHS 148C.

*Androecium*.—Present on disk florets only; five; synandrous.

*Staminal column*.—About 0.7 mm wide, about 6 mm long, not exserted; five fused stamens.

*Anthers*.—Fused, about 2 mm long and 0.5 mm diameter; color nearest RHS N199A.

*Filaments*.—Five; attached to column; thin, less than 0.2 mm diameter and 4 mm long; color nearest RHS NN155A.

*Pollen*.—Not observed.

*Gynoecium*.—On ray and disk florets; single; to 11 mm long.

*Style*.—Cylindrical; to about 5 mm long and 0.2 mm diameter; color nearest RHS NN155A.

*Stigma*.—Bifid; about 2 mm long and 0.1 mm diameter; color proximally nearest RHS 180B and distally nearest RHS 195B.

*Ovary*.—Inferior; obdeltoid; to 4 mm long and 2 mm wide at apex; color nearest RHS 146D distally and proximally nearest RHS NN155B.

*Fruit*.—Not yet observed.

Receptacle spines: With disk florets; acicular; narrowly acute apex; glabrous; lustrous; to 14 mm long and 2 mm across near middle; producing a cone about 45 mm wide and 30 mm tall;

Spine color: Adaxial and abaxial apices nearest RHS 183A, distal 2 to 3 mm nearest RHS 171A, middle portion between RHS 145A and RHS 146D, proximal portion translucent to nearest RHS 155D;

Disease resistance: Resistance and susceptibility beyond that of other hardy Coneflower cultivars have not been observed.

Growth: The plant grows best with plenty of moisture and adequate drainage but is able to tolerate some drought when mature.

Winter hardiness: At least from USDA zone 4 through 8.

I claim:

1. A new and distinct cultivar of *Echinacea* plant named 'Watermelon Sugar' as herein described and illustrated.

* * * * *